United States Patent
Guller (10) Patent No.: US 11,935,646 B1
(45) Date of Patent: Mar. 19, 2024

(54) PREDICTING MEDICAL DEVICE FAILURE BASED ON OPERATIONAL LOG DATA

(71) Applicant: Glassbeam, Inc., Santa Clara, CA (US)

(72) Inventor: Mohammed Guller, Danville, CA (US)

(73) Assignee: Glassbeam, Inc., Santa Clara, CA (US)

( * ) Notice: Subject to any disclaimer, the term of this patent is extended or adjusted under 35 U.S.C. 154(b) by 1142 days.

(21) Appl. No.: 16/365,205

(22) Filed: Mar. 26, 2019

Related U.S. Application Data (60) Provisional application No. 62/648,264, filed on Mar. 26, 2018.

(51) Int. Cl.
| | |
|---|---|
| *G16H 40/40* | (2018.01) |
| *G06F 16/2455* | (2019.01) |
| *G06N 5/02* | (2023.01) |
| *G06N 20/00* | (2019.01) |
| *G06Q 10/20* | (2023.01) |

(52) U.S. Cl.
CPC ......... *G16H 40/40* (2018.01); *G06F 16/2455* (2019.01); *G06N 5/02* (2013.01); *G06N 20/00* (2019.01); *G06Q 10/20* (2013.01)

(58) Field of Classification Search
CPC ......... G16H 40/40; G16H 50/20; G06Q 10/20
See application file for complete search history.

(56) References Cited

U.S. PATENT DOCUMENTS

| | | | | |
|---|---|---|---|---|
| 2015/0227838 | A1* | 8/2015 | Wang | G16H 40/40 706/12 |
| 2020/0371858 | A1* | 11/2020 | Hayakawa | G06F 11/0778 |

FOREIGN PATENT DOCUMENTS

| | | | | |
|---|---|---|---|---|
| WO | WO-2015125041 A1 | * | 8/2015 | ......... G06F 11/0706 |

OTHER PUBLICATIONS

Sipos, Ruben, et al. "Log-based predictive maintenance." Proceedings of the 20th ACM SIGKDD international conference on knowledge discovery and data mining. 2014. (Year: 2014).*

Patil et al. Predictive Modeling for Corrective Maintenance of Imaging Devices from Machine Logs. Conf Proc IEEE Eng Med Biol Soc. Jul. 2017.

Sipos et al. Log-Based Predictive Maintenance. KDD '14 Proceedings of the 20th ACM SIGKDD international conference on Knowledge discovery and data mining. Aug. 24-27, 2014.

Wang et al. Predictive Maintenance Based on Event-Log Analysis: A Case Study. IBM Journal of Research and Development. vol. 61, Issue 1, Jan., Feb. 2017.

\* cited by examiner

*Primary Examiner* — Jason B Dunham
*Assistant Examiner* — Constantine Siozopoulos
(74) *Attorney, Agent, or Firm* — Van Pelt, Yi & James LLP (57) ABSTRACT

Techniques are disclosed to predict medical device failure based on operational log data. Log data associated with a plurality of devices comprising a population of devices each having a same target part subject to failure. For each of at least a subset of the plurality of devices replacement dates on which the target part was replaced in that device are determined. A set of logged event data with prescribed severity is extracted from the log data for said plurality of devices. A subset of the logged event data is identified as being associated with impending failure of the target part. The subset of the logged event data is transformed into a normalized form. The normalized subset of the logged event data is used to generate a failure prediction model to predict failure of the target part in a device based on the current event logs from that device.

22 Claims, 9 Drawing Sheets

PREDICTING MEDICAL DEVICE FAILURE BASED ON OPERATIONAL LOG DATA

CROSS REFERENCE TO OTHER APPLICATIONS

This application claims priority to U.S. Provisional Patent Application No. 62/648,264 entitled PREDICTING MEDICAL IMAGING DEVICE FAILURE BASED ON OPERATIONAL LOG DATA filed Mar. 26, 2018 which is incorporated herein by reference for all purposes.

BACKGROUND OF THE INVENTION

Installed equipment may generate logs reflecting use and other events associated with the equipment, such as errors, warnings, part readings, etc. These logs may be sent (e.g., periodically, streamed in real time, etc.) to a central repository, e.g., for storage and/or analysis.

An example of installed equipment is medical equipment, such as medical imaging devices. The term "medical imaging device" refers to machines that are used to view the human body for diagnosing medical conditions. Examples of such device include X-Ray, Computed Tomography (CT), Magnetic Resonance Imaging (MRI), and Ultrasound machines. Other examples of medical equipment include defibrillator, EKG/ECG machine, patient monitor, anesthesia machine, X-Ray machine, digital mammography machine, nuclear medicine machine, PET-CT, etc.

A medical device has many parts that fail and may need to be replaced several times during its lifespan. The traditional approaches for handling part or component failure for medical devices include replacing a part when it fails (a reactive approach) or replacing a part on a predetermined maintenance schedule (a proactive approach). In the former case (replace on failure), the failure occurs at an unexpected time and can lead to extended down time (e.g., to obtain the part, to schedule the technician, etc.). In the latter case, the part may have material service life remaining at the time it is replaced.

BRIEF DESCRIPTION OF THE DRAWINGS

Various embodiments of the invention are disclosed in the following detailed description and the accompanying drawings.

DETAILED DESCRIPTION

The invention can be implemented in numerous ways, including as a process; a set of processes; an apparatus; a system; a composition of matter; a computer program product embodied on a computer readable storage medium; and/or a processor, such as a processor configured to execute instructions stored on and/or provided by a memory coupled to the processor. In this specification, these implementations, or any other form that the invention may take, may be referred to as techniques. In general, the order of the steps of disclosed processes may be altered within the scope of the invention. Unless stated otherwise, a component such as a processor or a memory described as being configured to perform a task may be implemented as a general component that is temporarily configured to perform the task at a given time or a specific component that is manufactured to perform the task. As used herein, the term 'processor' refers to one or more devices, circuits, and/or processing cores configured to process data, such as computer program instructions.

A detailed description of one or more embodiments of the invention is provided below along with accompanying figures that illustrate the principles of the invention. The invention is described in connection with such embodiments, but the invention is not limited to any embodiment. The scope of the invention is limited only by the claims and the invention encompasses numerous alternatives, modifications and equivalents. Numerous specific details are set forth in the following description in order to provide a thorough understanding of the invention. These details are provided for the purpose of example and the invention may be practiced according to the claims without some or all of these specific details. For the purpose of clarity, technical material that is known in the technical fields related to the invention has not been described in detail so that the invention is not unnecessarily obscured.

Techniques are disclosed to predict part failure based on log data. In various embodiments, statistical and/or machine learning techniques are used to determine whether a part needs to be replaced before it fails. In some embodiments, survival analysis is used to determine the average lifespan of a part. In some embodiments, a device is instrumented to collect a set of operating parameters or part readings of interest. Applying discriminant analysis techniques, a failure prediction model is trained on this data and then the model is used to determine whether the monitored parameters represent a part that is about to fail. In some embodiments, a Multi-Instance Learning algorithm is applied on all events logged by a device to training a failure prediction model.

In various embodiments, the task of predicting a part failure is transformed to a binary classification problem. Supervised machine learning techniques are applied on unstructured, semi-structured or multi-structured event logs generated by medical or other devices to train a classifier that is then used with new event logs to predict whether a component will fail soon.

In some embodiments, a part failure prediction system as disclosed herein includes three software applications. The first application identifies the events that can be used as the leading indicators of a part failure amongst the thousands of different types of events logged by a device. The second applications groups events by device and date, labels each group, engineers machine learning features from the leading indicator events and trains a binary classifier. The third application uses this binary classifier to offer a part failure prediction service. It takes new event logs as input and predicts whether a component will fail soon. In various embodiments, machine learning models are trained for different components in different types of medical devices.

In various embodiments, the following terms may be used and refer to the definitions and examples that follow:

SPL (Semiotic Parsing Language). SPL is an ETL (Extract Transform Load) language used to describe complex log formats and how to parse them.

LCP (Loader/Compiler/Parser). LCP is a framework watching inputs (files, streams, emails), chooses an SPL and compiles it into memory, and parses event logs.

Actors and Actor Framework. Actors and Actor Framework revolve around actors, which in various embodiments are lightweight, immutable processes each with their own message queue (mailbox). Actors can only interact with the outside world by passing and receiving messages. Messages are queued in the actor's mailbox in the order received, and the next message will be processed only when the current message is completed. Actors are asynchronous and thread-safe.

Message Queue and Message. A message is the smallest unit of work sent to an actor. Mailboxes are message queues attached to each actor, which receive messages sent to the actor by other actors or other processes. Messages are processed one at a time by an actor, though many actors can process messages from their own mailboxes asynchronously.

Figure 1:
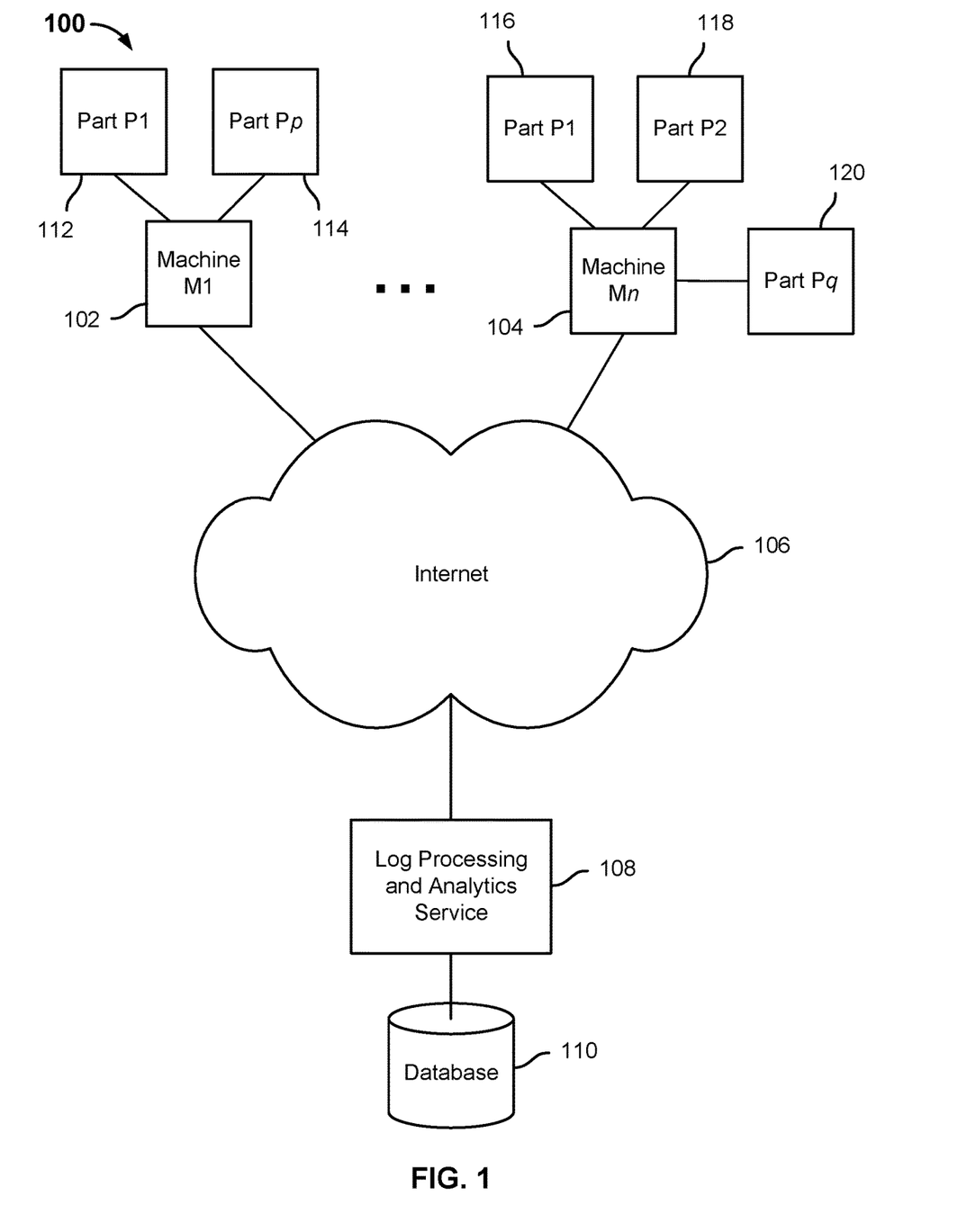
FIG. 1 is a block diagram illustrating an embodiment of a system to process and analyze log data.

FIG. 1 is a block diagram illustrating an embodiment of a system to process and analyze log data. In the example shown, a set of machines represented in FIG. 1 by machine 102 and machine 104 are configured to send log data via the Internet 106 to log processing and analytics service 108. Log processing and analytics service 108 parses log data receive from the machines (102, 104), extracts logged data, and stores the data in database 110.

In the example shown, the event logs received from the machines (102, 104) may include data that relates directly or indirectly to component parts of the machines (102, 104). For example, machine 102 includes two parts (112, 114) and machine 104 includes three parts (116, 118, 120). In some embodiments, each machine (102, 104) is configured to generate and stream (or otherwise send) via the Internet 106 to log processing and analytics service 108 event logs associated with use of the machine (102, 104) and its component parts (or other subcomponents and/or sub-systems). For example, machine 102 may be a medical diagnostic or treatment equipment. Each of the machine 102 and the parts (112, 114) may generate event logs.

In various embodiments, log processing and analytics service 108 is configured, as disclosed herein, to receive event log data from various machines (102, 104), e.g., machines of different types, manufacturer, etc.; extract data values associated with logged events; and store the extracted values in database 110. In some embodiments, search and/or analytics tools are provided to enable event log data to be searched and/or analyzed.

In various embodiments, log processing and analytics service 108 is configured, as disclosed herein, to provide a part failure prediction service. In some embodiments, the part failure prediction service is provided at another node or system having access to database 110, such as a dedicated remote server. In various embodiments, machining learning algorithms are applied to historical event log data in database 110 to train a part (or component) failure prediction model, which is then applied to current event logs from machines to predict (possible) part failure.

In various embodiments, arbitrary log data is process asynchronously and in parallel. In some embodiments, a framework disclosed herein is used to compile, asynchronously and if needed on demand, domain-specific language-based descriptions of complex log formats and how to parse them to generate compiled parsers that are stored in memory and which use an executable class plus actor structure to parse arbitrary log data asynchronously. In various embodiments, the framework may be implemented as a system, process, and/or embodied in a tangible, non-transitory computer readable storage medium, e.g., as a set of computer instructions to implement the framework.

In various embodiments, the framework may operate based on descriptions, expressed in a domain-specific language, of the format and/or content of logs generated by one or more systems. In some embodiments, SPL (Semiotic Parsing Language), an ETL (Extract Transform Load) language developed by Glassbeam, Inc., may be used to describe complex log formats and how to parse them. In some embodiments, a DSL and/or architecture as described in U.S. Pat. No. 9,830,368, the entire content of which is incorporated herein by reference as if fully set forth herein, such as the Semiotic Parsing Language (SPL) developed by Glassbeam, Inc., may be used.

In various embodiments, an LCP (Loader/Compiler/Parser) watches inputs (files, streams, emails), chooses a corresponding and/or otherwise suitable SPL (or other parser definition) program, and compiles the SPL into memory. In some embodiments, a context logic and/or module may determine a parser to be used to parse set of log data, e.g., a given file, bundle, stream, etc. The context module may use data included in the log data to determine which parser to use. For example, the context module may extract a part address, communication port, or other information from the log data, and map the extracted information to a serial number or other metadata, which in turn may be mapped to a parser definition of a parser to be used to parse the set of log data.

In various embodiments, Functional Programming concepts found in Scala, such as actors, maps, etc., as well as programming concepts such as threads, parallel (SMP) processing and containers, are used to provide and describe an asynchronous compiler as disclosed herein. In various embodiments, software in the Scala programming language running in the Akka framework is used to support a high level of actor-based concurrency. In various embodiments, fault tolerance is provided using this combination, or similar languages and concurrency models in a manner that enables high volumes of log data to be processed with minimal disruption. For example, if a chunk of log data is not able to be processed by a given actor, only that actor is interrupted. The actor may perform exception processing and be reset to be able to resume processing where it left off, all while other actors continue their respective work on other portions of the set of log data.

In some embodiments, a multi-tenant (Log File or Stream) log processing (e.g., LCP) system is provided. In various embodiments, the LCP is able to handle an arbitrary number of parser programs (SPL) and execute them in parallel.

In various embodiments, the LCP receives files, compiles the SPL (or other parser description) on-demand (unless already compiled & cached). In various embodiments, the log data processing system starts to parse the content even before compilation of the parser is complete (in various embodiments by employing a queuing mechanism and message bus, as disclosed herein). The resulting parsed data may be fed, asynchronously, to data stores (e.g., Cassandra, Solr, etc.), in some embodiments via a data abstraction object configured to translate parsed log data into a form required to store the data in the target data store.

Figure 2:
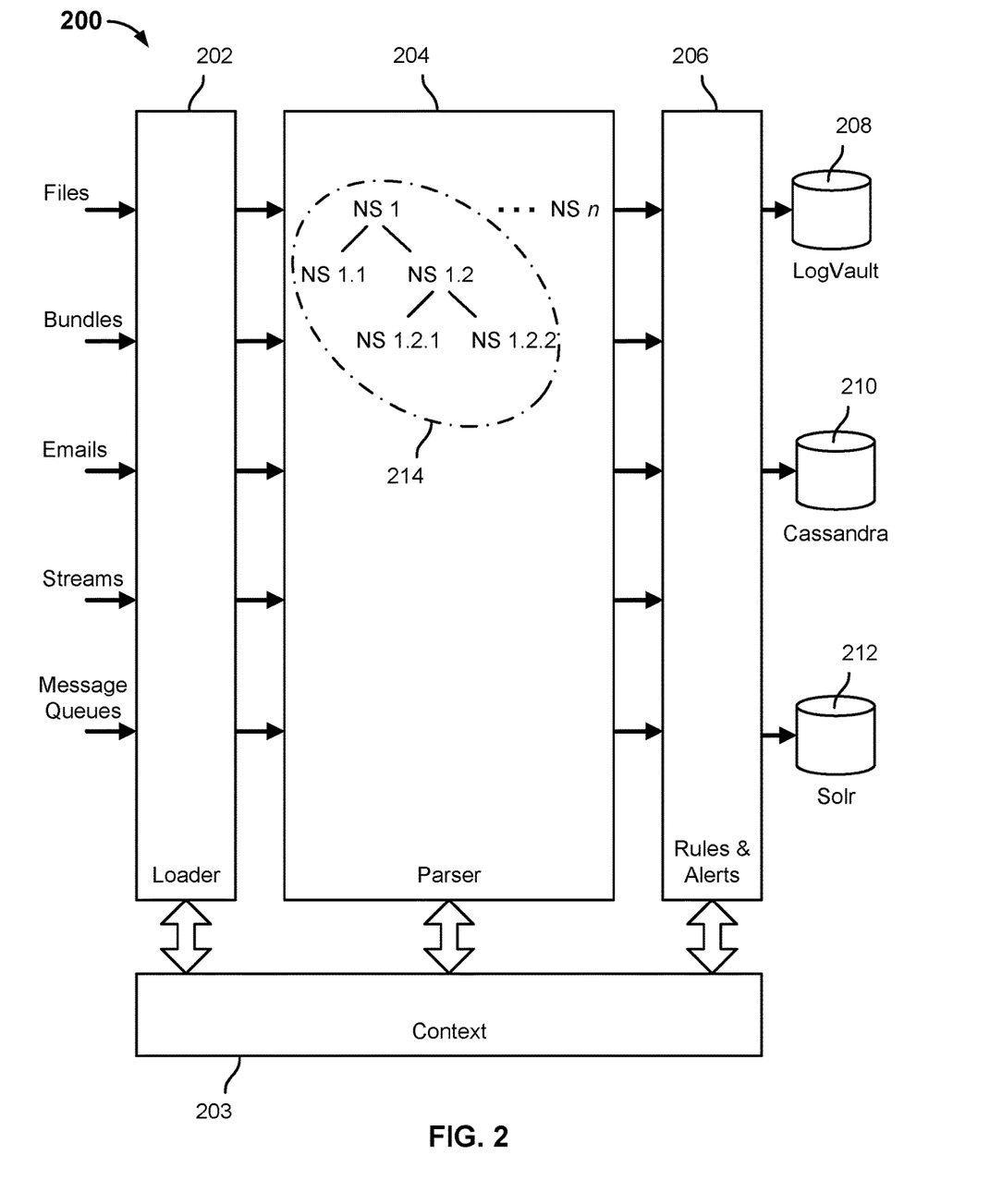
FIG. 2 is a block diagram illustrating an embodiment of a system to process and store log data asynchronously.

FIG. 2 is a block diagram illustrating an embodiment of a system to process and store log data asynchronously. In the example shown, the loader/compiler/parser (LCP) system 200 includes a loader component 202, a context module 203, a parser component 204, a rules and alerts component 206, and a plurality of data stores, including in this example a LogVault data store 208 (e.g., to store raw log data), a Cassandra database 210 (e.g., to store and process parsed log data, such as to facilitate analysis, reporting, etc.), and a Solr data store 212 (e.g., to provide full text search capability).

In various embodiments, each of the loader 202, the parser 204, and the rules/alerts 206 may include a plurality of "actor" entities, each of which is capable of acting independently of and in parallel with other actors comprising the system to load, parse, analyze (e.g. apply rules, generate alerts), and store log data from multiple sources and potentially in diverse forms (e.g., files, streams, etc.) asynchronously and in parallel. In various embodiments, a message bus infrastructure is provided to enable events and other messages to be transmitted between actors comprising the system 200. An actor may have an event or other queue in which log data and/or other data (e.g., messages, events) received via a message bus from other actors may be staged. Each actor may pull data from its queue to be processed.

In some embodiments, data not yet ready to be processed may be left in the queue until the condition(s) required to process the data is/are met. For example, in some embodiments, as described more fully below, parsing of a set of log data (e.g., a file, stream, etc.) may start before the system has finished compiling the parser. For example, a parser may have a hierarchical structure and may comprise one or more actors at each node in the hierarchy. The parser may be able to begin parsing certain log data, associated with nodes for which compilation of the required parsing elements (e.g., actors) has been completed, even while other log data remains held in a queue of the parser, waiting for compilation of parser elements associated with a subtree and/or node with which the other log data is associated to be completed.

In various embodiments, data from numerous and varied sources, and in various forms, may be received concurrently. For example, in the example shown in FIG. 2, log data is shown as being received (potentially) in the form of log files, bundles, emails, data streams, and message queues. In various embodiments, each set of log data is received and processed by one or more actors comprising loader 202. In various embodiments, context module 203 instantiates and/or configures actors comprising loader 202 to refine and/or augment log data by associating context data with received log data. For example, log data may arrive that is identified by a manufacturer's serial number. In some embodiments, the serial number may be used by context 203 to look up other information, such as a manufacturer name, product name, and/or schema (if multiple versions of log data structure may exist for the same product). In some embodiments, a data triplet comprising the manufacturer, product, and schema (M/P/S) may be used to characterize and processing log data. For example, a parser definition to be used to parse the log data may be determined based on the M/P/S determined to be associated with a received set of log data. In some embodiments, the M/P/S triplet may be used as and/or to generate a key to be used to store log data. In some embodiments, the M/P/S triplet or similar data may be used to ensure log data remains segregated in a multi-tenant environment, e.g., one in which multiple different system owners and/or users contract with the same multi-tenant instance of an LCP system such as system 200 of FIG. 2 to process log data from their respective installed product base. In various embodiments, the context 203 may provide the M/P/S or other identifying designation to the loader 202, parser 204, rules and alerts 206, and/or databases such as 208, 210, and 212, to ensure data remains segregated by manufacturer, end user, etc. While in some embodiments an M/P/S triplet may be used to identify and segregate data, e.g., by domain, owner, or otherwise, in various embodiments one or more other sets of data may be used, such as manufacturer/reseller (channel, etc.)/product, etc.

Referring further to FIG. 2, the parser 204 in various embodiments may include one or more instances of each of one or more different hierarchically-structured parsers. In some embodiments, a parser instance is created by compiling a corresponding parser definition that describes the content and structure of a log with which the parser definition is associated and how to parse instances of the log. In some embodiments, each parser may be associated with a top level "namespace" in the hierarchy. The namespace may correspond to and/or be associated with the manufacturer/product/schema triplet described above. In the example shown in FIG. 2, the parser 204 includes n parser instances, represented in FIG. 2 by top level namespaces "NS 1" and "NS n". In the example shown, the top level namespace "NS 1" is associated with a hierarchically structured parser 214, which includes multiple levels of hierarchy, each including zero or more child namespaces. For example, the top level namespace NS 1 includes child namespaces NS 1.1 and NS 1.2, and the latter in turn includes two child namespaces NS 1.2.1 and NS 1.2.2. In some embodiments, namespaces below the top level may correspond to different sections within a set of log data (e.g., a log file).

Each namespace in the hierarchy may be associated with one or more namespace "actors", each of which may be configured to perform such processing tasks as parsing and providing output data based on log data associated with the section (or other portion) with which that namespace is associated, and compiling the definition of the tables and/or child namespaces of that namespace. In some embodiments, each child namespace may represent a sub-section of log data. For example, the parser definition may define one or more tables within a namespace, and for each table may define one or more columns, column operations, other table functions, etc. In some embodiments, a namespace actor may be configured to compile definition statements associated with the namespace, e.g., to generate table structure information (e.g., schema), create table actors to process associated log data, and create child namespaces (if any), including associated actors. In some embodiments, a parser definition may for indicate for each of at least a subset of table elements a corresponding type of parser to be used to parse associated data. For example, if a sub-section of log data with which a table is associated comprises free text, a line-by-line parser may be used. If instead the subsection included XML data, a parser optimized to parse XML may be used. Other examples include parsers optimized to parse name-value pairs, JSON, CSV, or other types of format of log data. In various embodiments, creating an actor may include creating data structures, such a queue in which to stage events or other messages received by the actor, and one or more message buses to be used to send messages to other actors in the system.

In various embodiments, actors are used in loader 202 to receive sets of log data, instantiate parsers, and stream log data (e.g., line by line, in case of log data received other than as a stream) to corresponding parsers. In some embodiments, loader 202 and parser 204 are configured to load and parse log data, as disclosed herein, e.g., to identify and extract features and create labeled datasets to be used to create and apply part failure prediction models as disclosed herein.

In various embodiments, complex software, hardware, and/or combined system may comprise many components, one or more of which may have multiple instances. In some systems, each component (instance) could be working independently within the whole system thus having its own time-ordered sequence of log events. Though such systems may have a hierarchy in the way they are built, the logging itself may not be hierarchical—because multiple components may be working in parallel at any given point of time. In such systems logging is separated out for each component (instance). The system as a whole ends up having multiple log files/streams.

In various embodiments, a parsing platform, such as parser 202, is built using the Scala programming language and the Akka actor framework. Scala and Akka are a very powerful toolkit to build fast data platforms which use multiple threads and CPU cores very efficiently. Techniques disclosed herein are implemented using multiple actors. Each actor does a small chunk of work and sends a message to the next actor in the pipeline. Akka allows having 'n' instances of any particular type of actor—this capability along with actors leads to fast concurrent parsing.

In various embodiments, an architecture and environment as shown in FIGS. 1 and 2 is used to extract and store log data to create and/or apply a part failure prediction model as disclosed herein. However, in various other embodiments, other techniques may be used to obtain an at least partially structured set of log data to be used to train and/or apply a part failure prediction model as disclosed herein.

Installed equipment may play a crucial role in an industry. For example, in the medical field, medical devices such as X-ray, Computed Tomography (CT), Ultrasound, and Magnetic Resonance Imaging (MRI) devices allow health care providers to see inside the body of their patients and help determine the root cause of their symptoms. Thus, they enable healthcare providers to develop the right treatment plan for their patients.

However, these medical devices (and other equipment) are not only expensive but also have parts that fail multiple times during the lifespan of a device. Generally, a replacement part is ordered when a part fails. However, it may take up to a few days for a replacement part to arrive. Until then that device cannot be used. Thus, an expensive asset stays unutilized because of an unplanned downtime. Alternatively, critical parts are replaced on a predetermined maintenance schedule. While this approach reduces unplanned downtime, it does not eliminate unplanned downtime since a part can fail between scheduled maintenance visits. In addition, it causes waste since a non-problematic part will also be replaced at a predetermined schedule.

In various embodiments, log processing and machine learning techniques disclosed herein are used to proactively determine when a part needs to be replaced. Machine learning techniques are applied on unstructured, semi-structured or multi-structured event logs generated by a medical device (or other equipment) to predict whether one of its components will fail soon.

Generally, event logs are used for troubleshooting a device if there is a problem or the device does not function correctly. An event log file contains device and runtime information deemed important by a developer of the software running on it. In most cases, event logs are saved in a text file in a human-readable format. Each event log has a descriptive text describing an event or providing some information and is tagged with a severity, date/time stamp and source of the event. The severity of an event indicates whether it contains debugging, informational, warning or error information. The event description is generally unstructured or free-flowing text. A device may log tens or hundreds of thousands or even millions of events every day.

In various embodiments, a subset of these events is used to train a predictive machine learning model. Specifically, error and warning events logged by a device are used to identify leading indicators of a part failure and engineer machine learning features. These events are labeled programmatically to indicate whether they represent events from a device that will experience part failure soon. A labeled structured dataset is generated from unlabeled unstructured, semi-structured or multi-structured event logs. This dataset is then used with supervised machine learning algorithms to fit or train models. The best model is used for predicting whether a part will fail soon based on the current or most recent event logs generated by a device. The disclosed approach is used, in various embodiments, to predict failure of any part in any type of medical devices (or other equipment) from any device manufacturer.

In some embodiments, by way of example, the failure of an X-ray tube in a CT scan machine is predicted. The steps for training and using a model that predicts tube failures are as follows, in some embodiments:

1) Collect historical event logs from several CT scanners. This data must include logs from CT scanners whose x-ray tubes stopped functioning correctly and had to be replaced.
2) Parse the unstructured, semi-structured or multi-structured events into a structured dataset that includes the following columns, event timestamp, event severity, event source, and event description, and the id of the device that logged that event.
3) Extract replacement dates for X-Ray tubes from the logs or import from an external system such as a CMMS (Computerized maintenance management system) or some other system used to provide maintenance support for these devices.
4) Identify the unique event types from the corpus of all events and map free-flowing event descriptions to unique event types. A log file containing millions of events may have only a few hundred different event types. The same event may be logged multiple times with different timestamps. Similarly, an event may be logged several times with different dynamic runtime parameters. Thus, the same source code line generates many variants of the same event at run-time. Even though these events do not have identical description text, they have the same static part of the event description. They all belong to the same event type.
5) Filter the warning and error events.
6) Identify the event types that can be used as leading indicators of an X-Ray tube failure (see, e.g., FIG. 6). These event types are the symptoms of an unhealthy X-Ray.
7) Group the events by CT scanner id and date. This will result in creation of a collection of event groups, where an event group contains all the events generated by a CT scanner on some date. For example, if there are logs for sixty days from each of hundred CT scanners, this step will create 6000 event groups.

8) Count the occurrences of each leading indicator event type in each event group. These counts can be stored in a logical table, where each row represents an event group. The combination of CT scanner unique identifier (device id) and date forms the primary key of a row in this logical table. In addition to the device id and date columns, this logical table will have as many columns containing counts as the number of leading indicator event types.

9) Generate features for machine learning by performing aggregation operations such as SUM, AVERAGE, MAX, MIN, etc., on the leading indicator event type count columns for each device over a sliding window of configurable duration. For example, this window could be 5, 10 or 15 days. The window duration is based in some embodiments on how many days prior to complete breakdown of an X-Ray tube, a scanner starts logging symptoms of an unhealthy X-Ray tube. The sliding window advances by one day at a time over rows ordered by date.

Figure 8:
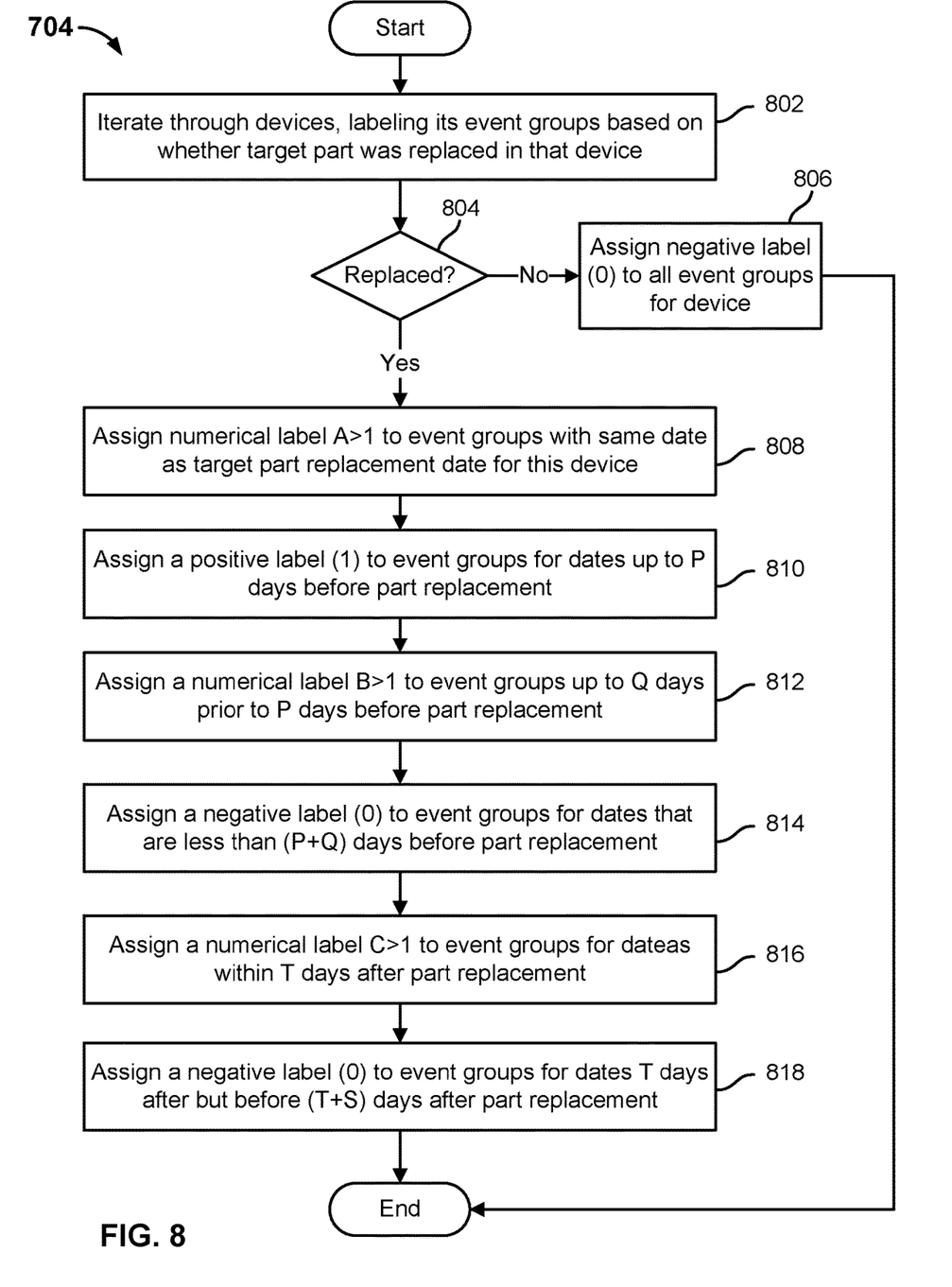
FIG. 8 is a flow chart illustrating an embodiment of a process to label event groups comprising log data.

10) Label each event group (e.g., as illustrated in FIG. 8). An event group with positive label represents a scanner with an unhealthy X-Ray tube that will fail soon. Negative label indicates that an event group represents events from a scanner whose X-Ray tube will not fail soon.

11) Filter the event groups that have label as 0 (negative) or 1 (positive).

12) Split the labeled event groups into a training dataset and a test dataset.

13) Using the features and labels generated in previous steps, fit machine learning models on the training dataset using different machine learning algorithms available for training a binary classifier. For example, in some embodiments models are trained with one or more of Naïve Bayes, Logistic Regression, SVM, Random Forest, Gradient Boosted Trees and Deep Neural Networks. Find optimal hyper-parameters for each ML algorithm using cross-validation.

14) Evaluate the models trained in previous step on the test dataset using performance metrics such as accuracy, recall, precision, F1-score and AuROC.

15) Select the model giving the best performance on the test dataset.

16) Evaluate best model's performance on test dataset against business requirements or the minimum performance metrics that need to be met for a model to be eligible for deployment.

17) Deploy or operationalize the best model using a data pipeline implemented for ML scoring or inference. The model takes as input daily logs generated by a CT scanner and returns a prediction whether its X-Ray tube will fail soon.

18) Continue to update ML model periodically by updating the features set and adding more positive samples to the training dataset.

While the above example refers to use of techniques disclosed herein to predict failure of an X-Ray tube in a CT scanner, in various embodiments techniques disclosed herein are used to train a failure prediction model based on event log data for other parts in a CT scanner or from other types of medical devices or other equipment and to use the model to predict part failure before failure occurs.

Figure 3:
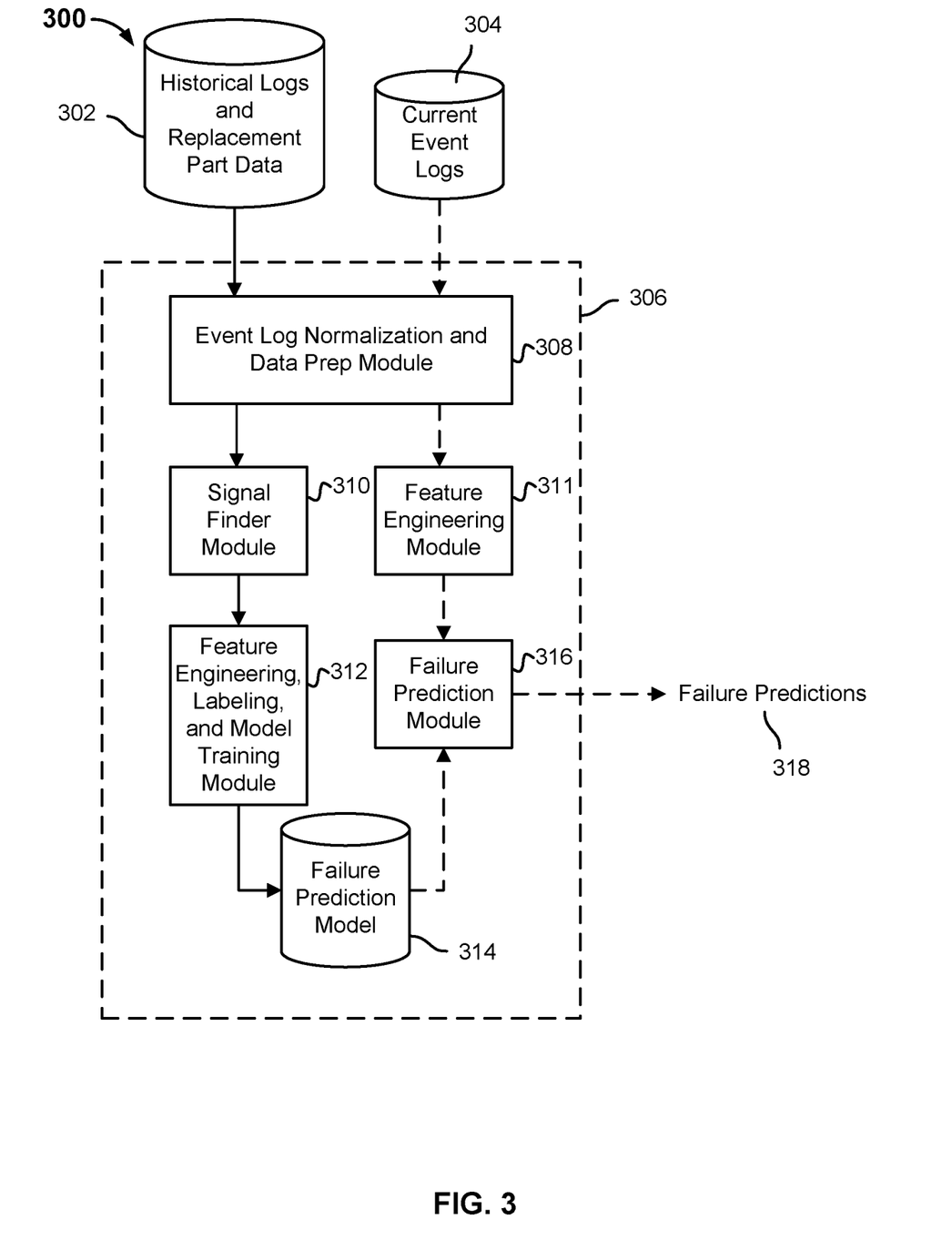
FIG. 3 is a block diagram illustrating an embodiment of a failure prediction system.

FIG. 3 is a block diagram illustrating an embodiment of a failure prediction system. In the example shown, system 300 includes a failure prediction server, system, and/or service 306 that receives training data 302 comprising log data associated with instances of a given machine, device, etc. within a population of related machines, devices, etc., such as a CT scanner or other medical equipment of a given make and model, along with part replacement data for at least a subset of the machines, etc., in which a given part for which a failure prediction model is to be generated has failed and been replaced.

In addition, failure prediction server, system, and/or service 306 is configured to receive current log data 304 from machines, devices, etc. comprising the population and/or a related set of machines, devices, etc., such as another population of machines of the same make and model. In various embodiments, failure prediction server, system, and/or service 306 is configured to use a part failure prediction model it generated based on training data 302 to predict based on current log data 304 whether the part for which the part failure prediction model was generated is predicted to fail in a given instance of the machine, device, etc., e.g., within a prediction period or window. In various embodiments, part failure predictions may be used to proactively order replacement part and/or optionally schedule replacement service prior to failure.

In the example shown, failure prediction server, system, and/or service 306 includes an event log normalization and data prep module 308. In this example, historical log data received as training data 302 or current log data 304 is normalized and pre-processed to train and/or apply a part failure prediction model as disclosed herein. In some embodiments, for example, log data is normalized to a format not specific to any machine, make, or model, enabling the failure prediction server, system, and/or service 306 to be used to train and/or apply a part failure prediction model for any part of any machine, device, etc., regardless of type, make, or model. In various embodiments, the event log normalization and data prep module 308 receives log data as stored in a structured database and generates a filtered set of structured event log data to be used to train and/or apply a part failure prediction model as disclosed herein.

In the model generation (training) phase, in various embodiments, event log normalization and data prep module 308 extracts or otherwise receives and/or determines part failure and/or replacement dates for the part for which a failure prediction model is being generated.

In the model generation (training) phase, in various embodiments, the signal finder module 310 analyzes event log data to identify a filtered set of events that occurred (or not) in prescribed windows before and after part replacement. Events potentially predictive of part failure are identified as signals or leading indicators of part failure. Features used by machine learning algorithms to train a model are engineered from these signals.

Failure prediction server, system, and/or service 306 further includes a feature engineering, labeling and model training module 312 that engineers features from and labels the events associated with the event types identified as potentially predictive of part failure. In the model training phase, the feature engineering, labeling and model training module 312 applies multiple different machine learning algorithms to the labeled dataset to train a failure prediction model 314 for a part. In the failure prediction phase, the feature engineering module 311 generates features from the current event logs of a device and provides the features as input data to the failure prediction module 316, which uses the feature data and failure prediction model 314 to determine whether the part is predicted to fail in a given instance of the machine, device, etc., based on the feature data for that instance and the failure prediction model 314. If a failure is predicted 318, one or more configured actions are taken—e.g., an alert or other notification—is generated and sent, e.g., to an administrator, to a system or module configured to automatically start a workflow to proactively order a replacement and optionally schedule a technician to replace the malfunctioning part, etc.

Figure 4:
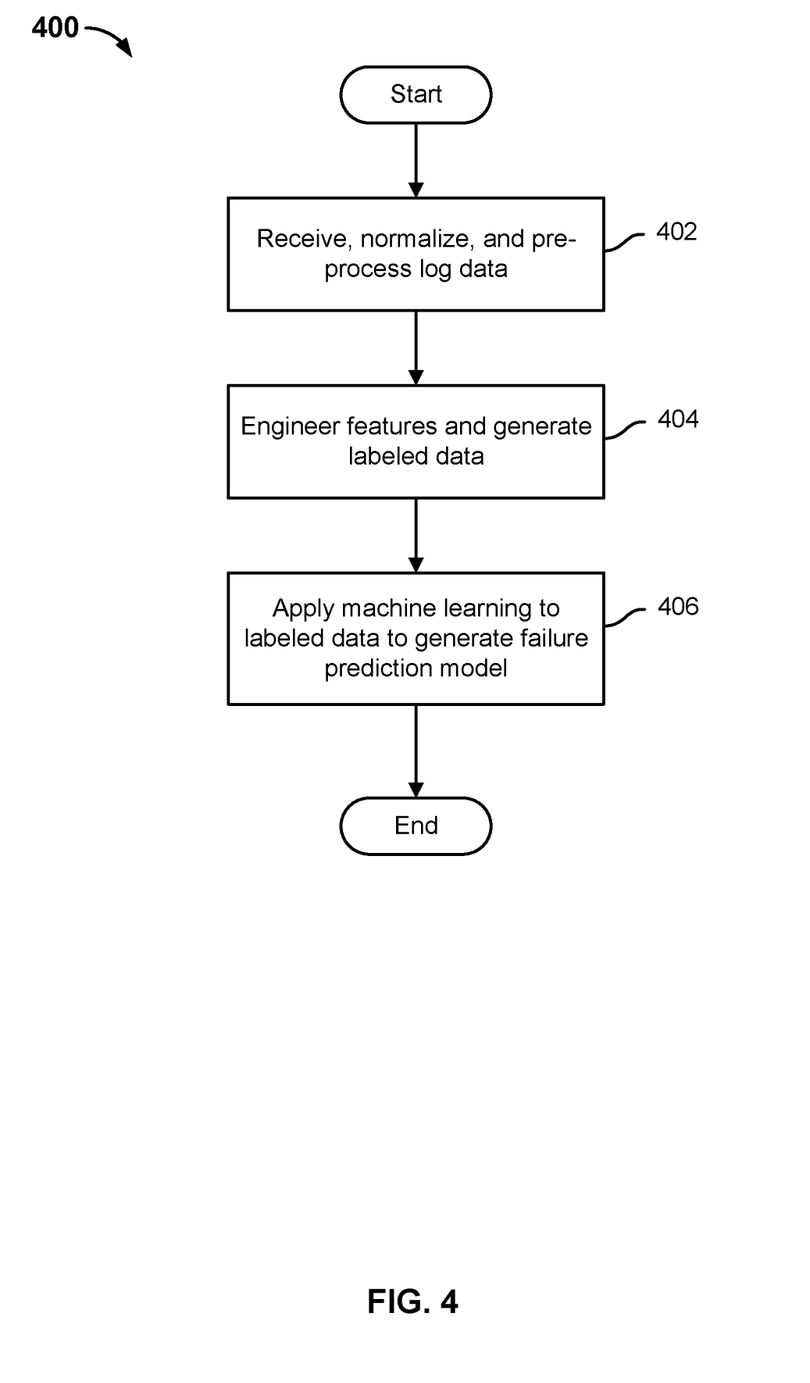
FIG. 4 is a flow chart illustrating an embodiment of a process to predict failure based on log data.

FIG. 4 is a flow chart illustrating an embodiment of a process to predict failure based on log data. In various embodiments, the process 400 of FIG. 4 is implemented by one or more computers, such as one or more servers configured to provide a part failure prediction service as disclosed herein. For example, in some embodiments, the process 400 of FIG. 4 is implemented in whole or in part by a log processing and analytics service, such as log parsing and analytics service 108 of FIG. 1.

In the example shown, at 402 log data is received, normalized, and pre-processed to determine and store a subset of log data, e.g., a subset of logged events, to be used to generate (train) a part failure prediction model. At 404, data comprising a set of "features" to which machine learning algorithms are to be applied to generate a part failure prediction model are engineered and labeled. At 406, machine learning algorithms are used to generate a part failure prediction model based on the datasets extracted and labeled at 404. In various embodiments, a plurality of machine learning algorithms including two or more different types of machine learning algorithm are applied each to a training subset of the labeled data to generate a corresponding model. The models are then tested using a test subset of the labeled data and a "best" model is selected, e.g., one that best predicts failures among the test subset of machines/devices.

Figure 5:
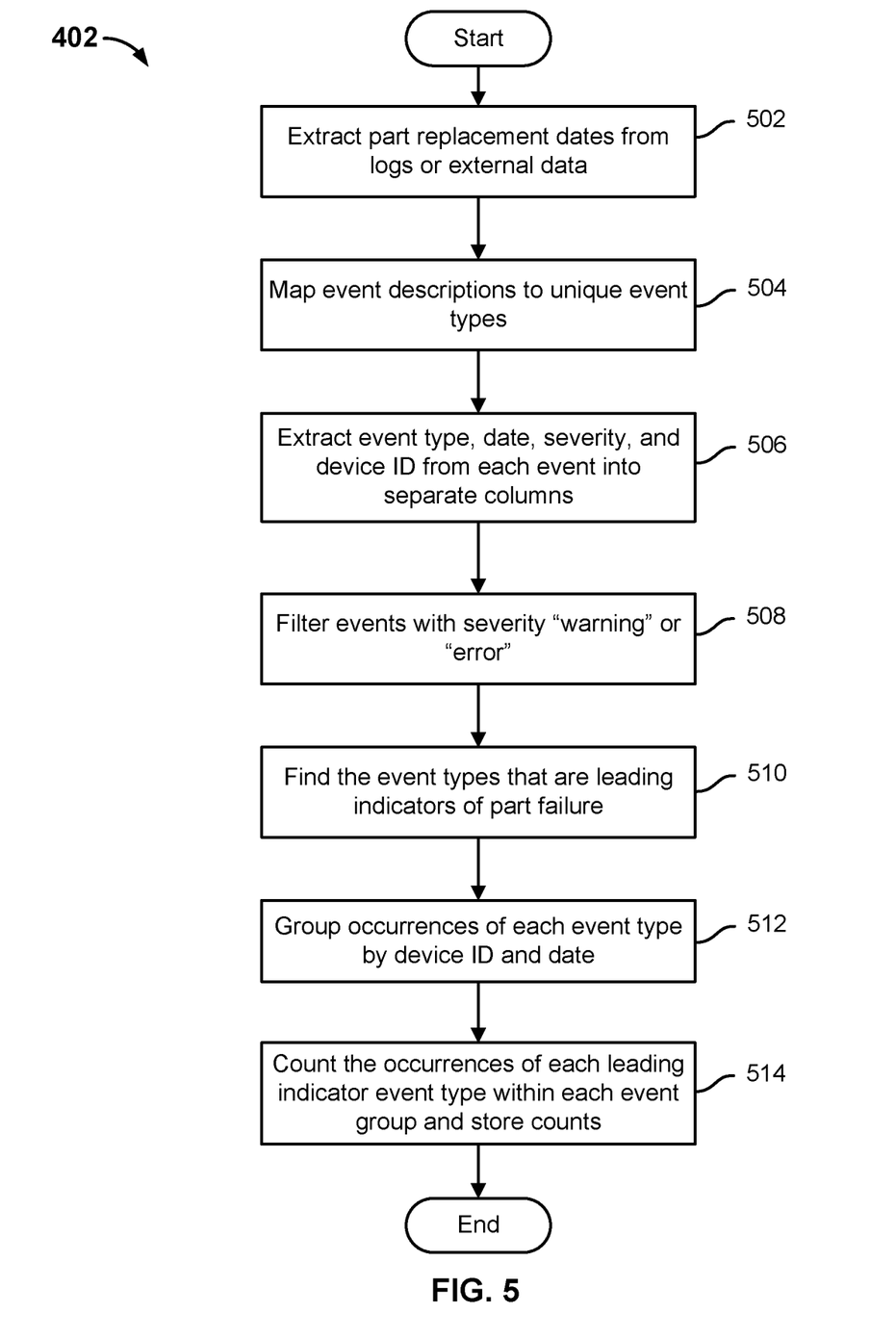
FIG. 5 is a flow chart illustrating an embodiment of a process to receive, normalize, and pre-process log data.
Figure 6:
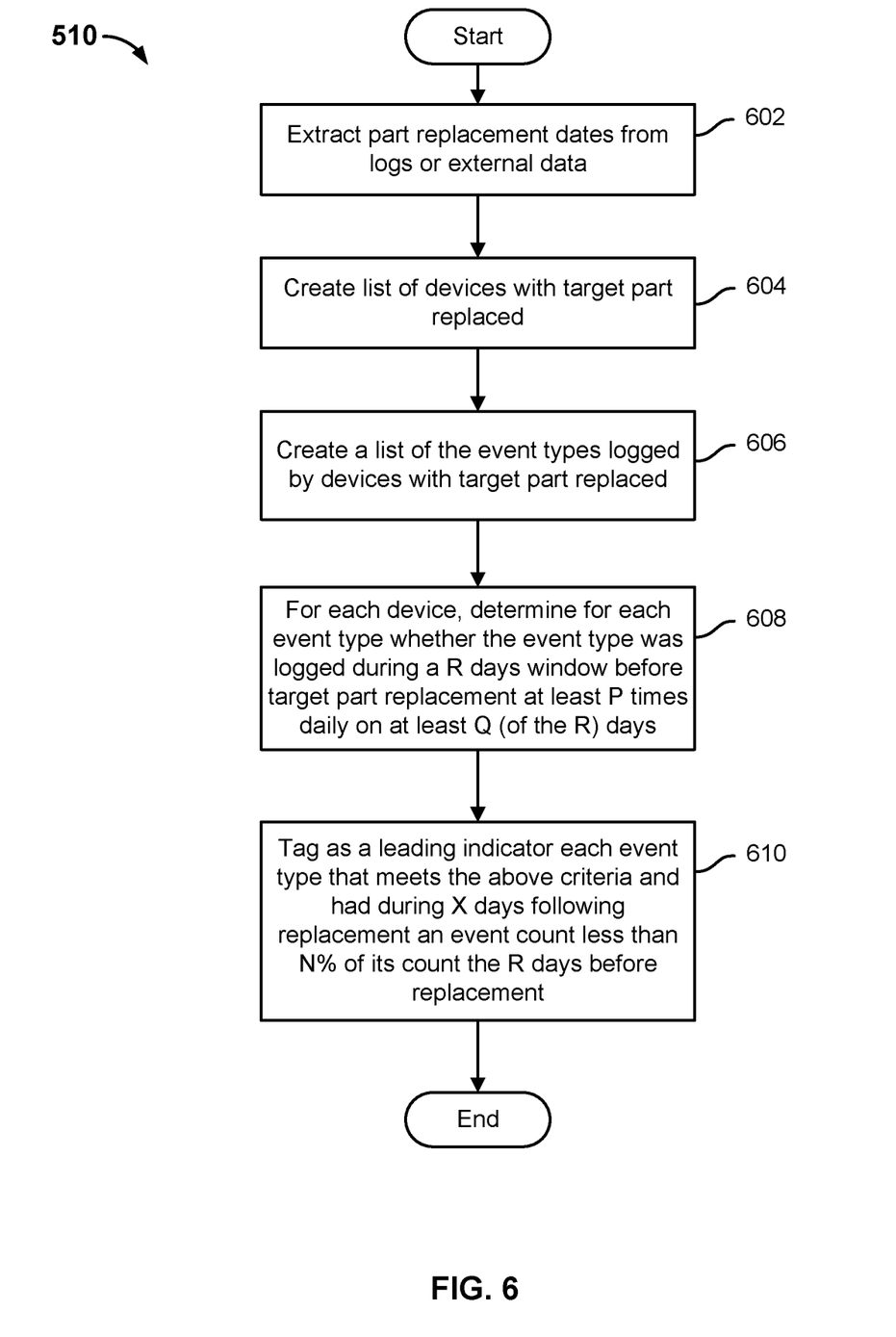
FIG. 6 is a flow chart illustrating an embodiment of a process to identify a subset of logged event types as leading indicators of failure.

FIG. 5 is a flow chart illustrating an embodiment of a process to receive, normalize, and pre-process log data. In various embodiments, step 402 of FIG. 4 is implemented at least in part by the process of FIG. 5. In the example shown, at 502 part replacement data is extracted from received logs and/or external data, such as data from a maintenance log or management system. At 504, event descriptions are mapped to unique event types. For example, events of the same type may share common content but not be entirely identical, e.g., due to non-static info included in the event description such as temperature, etc. At 506, event type, date, severity (e.g., warning, error, etc.) and unique device identifier information is extracted from each logged event and stored in separate columns. In some embodiments, a separate table or other data structure is created and used to store the values extracted at 506. Events with severity of "warning" or "error" are filtered at 508, to provide a subset of events having the prescribed severity or greater in this example. At 510, event types that are leading indicators of part failure are determined. In some embodiments, the process of FIG. 6 is used. In various embodiments, events that occur across many devices with at least a prescribed frequency of occurrence in a prescribed window (e.g., a certain number of days within a prescribed number of days before part replacement) and which occur less or not at all during a second window of prescribed number of days after part replacement may be identified as a leading indicator event type. At 512, occurrences of each event type are grouped by device identifier and date. At 514, the number of occurrences of each leading indicator event type within each event group (by device and date) are counted and stored.

In various embodiments, the process of FIG. 5 is implemented to filter and pre-process log data in preparation to engineer features and label datasets to be used to train and test a part failure prediction model as disclosed herein.

In various embodiments, once a part failure prediction model has been created at least in part based on application of the process of FIG. 5 to historical log data, some of the steps of the process of FIG. 5 are performed on new or current log data, to prepare such data to be evaluated using the part failure prediction model to detect (possible) impending failures. For example, the steps other than step 502 and step 510 may be performed, since the features to be extracted would in some embodiments be the same ones determined at model generation time to be (potentially) predictive of part failure.

FIG. 6 is a flow chart illustrating an embodiment of a process to identify a subset of logged event types as leading indicators of failure. In various embodiments, the process of FIG. 6 is performed to implement step 510 of the process of FIG. 5. In the example shown, at 602 part replacement dates are extracted from log data and/or one or more external sources. At 604, a list of devices in which the targeted part—i.e., the part for which a part failure prediction model is currently being created—has been replaced is created. At 606, a list is created of event types logged by devices in which the part has been replaced. At 608, for each device, it is determined for each event type observed (at 606) in devices in which the part has been replaced whether the event type was logged during an R days window prior to the part being replaced with a frequency, distribution, etc. that satisfies a prescribed criteria, in this example the criteria being that the event type was logged at least P times daily on a least Q of the R days comprising the window. In various embodiments, the length of the window R, the start/end days prior to replacement for the window R, and the frequency/other criteria are determined based at least in part on log data associated with devices in which the target part was replaced. At 610, each event type that meets the pre-replacement criteria (at 608) is tested against criteria for occurrence (logging) of the event type post-replacement. In this example, an event type is determined to be a "leading indicator" of part failure if the pre-replacement criteria tested at 608 are met and the event type had during X days following replacement an event count less than N % of its corresponding count during the R day window prior to replacement.

In various embodiments, the criteria applied at 608 and/or 610 may be adjusted and/or determined by domain experts and/or at least in part by reviewing log data of at least a sample of devices in which the target part has been replaced. The criteria depend on the type, make, and model of a device as well as the type of the part for which a model is being trained. For example, some type of devices may start logging failure symptoms two weeks before a part needs to be replaced whereas another type of devices may start logging symptoms only a week before a part needs to be replaced. The criteria also depend on how quickly a part deteriorates after the onset of symptoms of a problem with that part.

Figure 7:
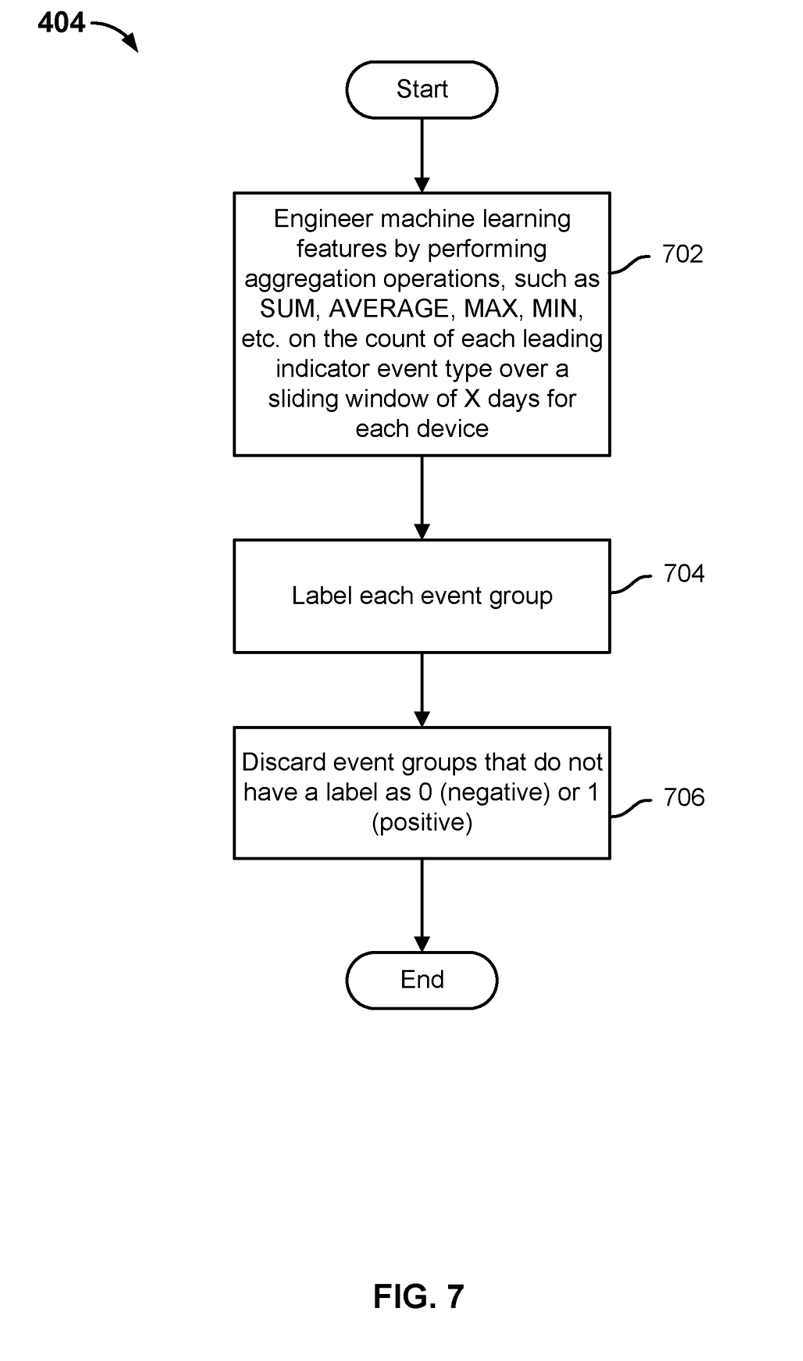
FIG. 7 is a flow chart illustrating an embodiment of a process to engineer features from and label log data.

FIG. 7 is a flow chart illustrating an embodiment of a process to engineer features from and label log data. In various embodiments, the process of FIG. 7 is used to implement step 404 for FIG. 4. In the example shown, at 702, machine learning features are engineered by performing aggregation operations, such as SUM, AVERAGE, MIN, MAX, etc., on the count of each leading indicator event type over a sliding window of X days for each device. Each event group is labeled at 704. As described earlier, an event group represents the counts of different leading indicator event types logged by a device on a given day. In some embodiments, event groups are labeled as shown and described in connection with FIG. 8. At 706, event groups that do not have a label as 0 (negative) or 1 (positive) are discarded.

In various embodiments, the processes of FIGS. 5, 6 and 7 enable log data from a variety of different devices, e.g., different manufacturers, different types of device, different make, model, build, etc., to be processed as disclosed herein using a shared framework not specific to any one device. For each device type, log data is processed to programmatically identify unique event types, map events descriptions to unique event types, identify the event types associated with predicting failure (leading indicator event types), group events into event groups (e.g., one group) per device identifier and date, label the event groups, and filter and aggregate logged event data to focus on a subset of data useful to predict failure. In various embodiments, unique event types are identified and logged events are aggregated and filtered programmatically without a priori knowledge of device attributes, log format or content, etc. Features are engineered programmatically to produce datasets usable to create without human intervention failure prediction models as disclosed herein, and to use such models to predict failure in devices (system) in which the target part (component) will need to be replaced within a prescribed prediction window.

FIG. 8 is a flow chart illustrating an embodiment of a process to label event groups comprising log data. In various embodiments, the process of FIG. 8 is performed to implement step 704 of FIG. 7. In the example shown, the process of FIG. 8 is performed iteratively through all applicable devices (device IDs), labeling event group data for each device based on whether the target part was replaced in that device (802). If the part was not replaced in the device (804), a negative label (0) is assigned to all event groups for that device. If the part was replaced in the device (804), the following steps are performed:

- at 808, a numerical label A>1 is assigned to event groups with the same date as target part replacement for that device;
- at 810, a positive label (1) is assigned to event groups for dates up to P days before target part replacement;
- at 812, a numerical label B>1 is assigned to event groups up to Q days prior to P days before target part replacement;
- at 814, assign a negative label (0) to event groups for dates that are less (earlier) than (P+Q) days before part replacement;
- at 816, assign a numerical label C>1 to event groups for dates within T days after target part replacement;
- at 818, assign a negative label (0) to event groups for dates T days after but before (T+S) days after part replacement.

In various embodiments, the values A, B, and C in the process of FIG. 8 are used to segment the event groups into various categories comprising event groups that are not used. In some embodiments, event groups with label A or B are not used because of the uncertainty about the health of a device (or part) on certain dates. For example, event groups with label A may represent events that occurred after replacement or before replacement depending on whether a part was replacement at the beginning or end of day; event groups with label B may represent a buffer zone where one cannot be sure whether event groups come from a device with either healthy or malfunctioning part; etc. Event groups with label C are not used in some embodiments because of how the algorithm works. Since features are generated by performing aggregation operations on the event counts over a window of prescribed duration, the event counts just before replacement date will affect the features generated for the dates immediately after a part replacement date.

Figure 9:
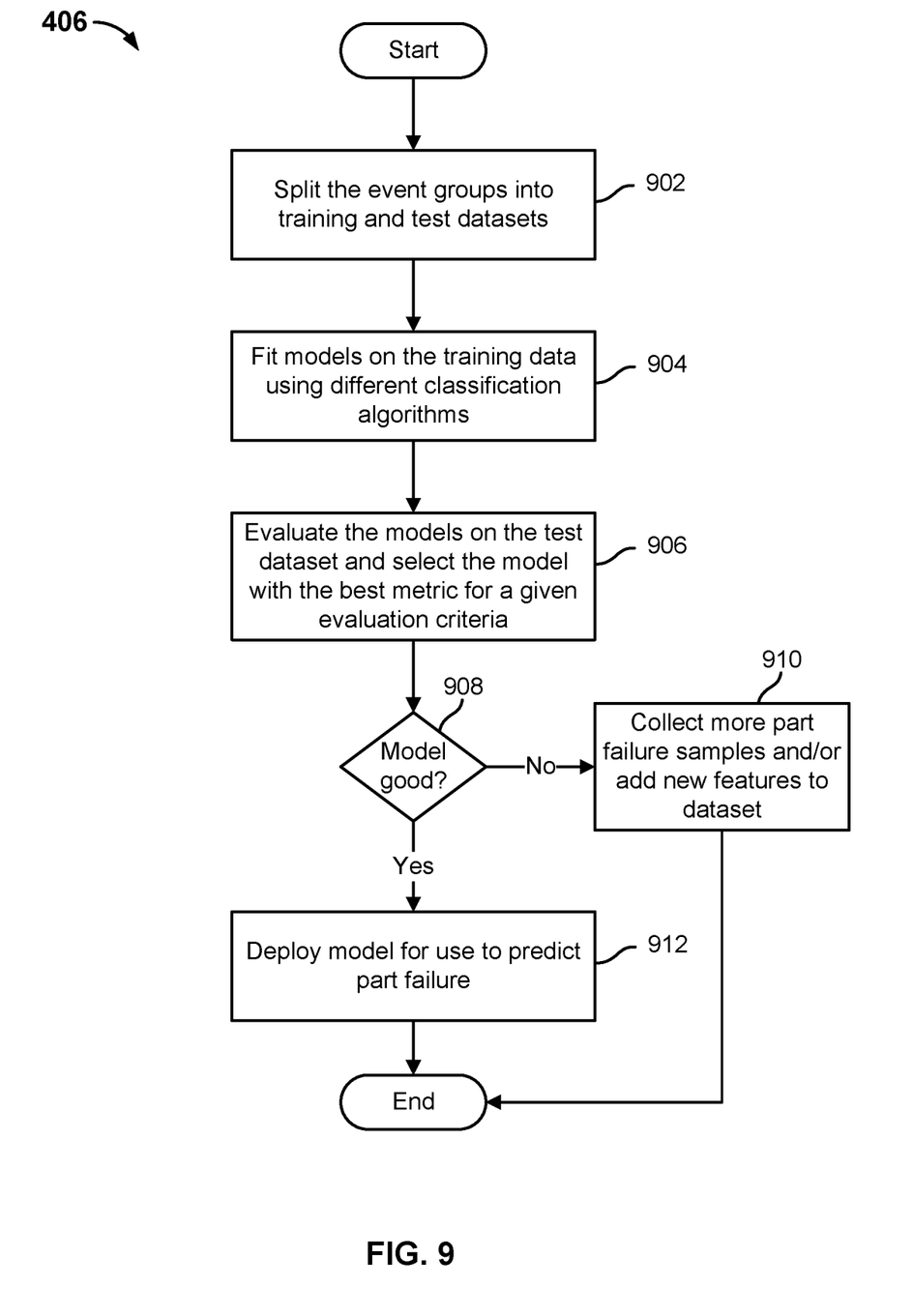
FIG. 9 is a flow chart illustrating an embodiment of a process to apply machine learning techniques to log data to generate a failure prediction model.

FIG. 9 is a flow chart illustrating an embodiment of a process to apply machine learning techniques to log data to generate a failure prediction model. In various embodiments, the process of FIG. 9 is performed to implement step 406 of FIG. 4. In the example shown, at 902, event groups are split into training and test datasets. For example, the labeled events groups for one set of devices may be included in the training set and the labeled event groups for the remaining devices may be included in test dataset. The test dataset is used, in various embodiments, to test the various models generated by the respective machine learning algorithms to select a model having desired performance, e.g., highest recall or F1-score on the test dataset.

At 904, models are fitted on the training data using different classification (machine learning) algorithms. At 906, the resulting models are evaluated based on their performance on the test dataset and the model with the best metric for a given evaluation criteria is selected. If none of the models satisfies prescribed selection criteria (908), at 910 more part failure samples are obtained and/or additional features are added to the datasets and the process of FIG. 9 is performed again. If the model selected at 906 meets applicable criteria (908), at 912 the model is deployed for use to predict target part failure in devices based on their current event logs.

While in various embodiments described herein reference is made in some detail to generating and using a model to predict failure of a single target part in a single device and/or device type (e.g., machine, make, model), in various embodiments techniques disclosed herein are applied across tenants, customers, device type (machine, make, model), etc., and with respect to zero, one, or more parts for each device type, etc. For example, CT scanner X-Ray tube failure prediction models may be generated for a single customer's installed base of CT scanners of a given make and model. In some embodiments, CT scanner X-Ray tube failure prediction models may be generated for each of a plurality of CT scanner types (e.g., different makes and/or models), in some embodiments across multiple users/owners of the same make/model. In some embodiments, models are generated and used as disclosed herein to predict failure of parts other than and/or in addition to X-Ray tubes or similar parts. In some embodiments, models are generated and used as disclosed herein to predict failure of parts in other types of medical devices such as Magnetic Resonance Imaging (MRI) machine, Ultrasound machine, Defibrillator, EKG/ECG machine, Patient Monitor, Anesthesia machine, X-Ray machine, Digital mammography machine, Nuclear medicine machine, etc. In some embodiments, techniques disclosed herein are used to predict failure of non-hardware components, such as software applications, modules, or components.

In various embodiments, techniques disclosed herein may be used to generate a failure prediction model for a target part (or component), and to use the model to predict failure and take proactive action (e.g., order replacement part, schedule a technician, and/or replace the part) prior to actual failure.

Although the foregoing embodiments have been described in some detail for purposes of clarity of understanding, the invention is not limited to the details provided. There are many alternative ways of implementing the invention. The disclosed embodiments are illustrative and not restrictive.

What is claimed is:

1. A system, comprising:
a communication interface configured to receive log data associated with a plurality of devices, the plurality of devices comprising a population of devices of a same device type each having a same target part subject to failure and the log data for each of at least a subset of the devices comprising ten thousand or more logged events per day; and
a processor coupled to the communication interface and configured to:
   determine based on the received log data, for each of at least a subset of the plurality of devices, a replacement date on which the target part was replaced in that device;
   parse the received log data to generate a structured dataset that includes for each device a plurality of sets of structured event data, each set of structured event data including for an event with which that set of structured event data is associated at least an event severity and an event description;
   use the structured dataset to extract from the log data for said plurality of devices a set of structured logged event data with prescribed severity, each logged event in the set having a corresponding event type, the event type being determined at least in part by processing the event description data comprising the structured dataset to determine that a static portion of the data comprising the event description of the logged event is associated with the event type;
   identify programmatically a subset of the logged event data as being associated with impending failure of the target part, at least in part by determining for each event type with respect to each device in said plurality of devices whether an event of that event type was logged for that device with a first prescribed daily frequency or number of occurrences within a first window before replacement of the target part in that device and determining that events of that event type were logged as having occurred with less than a second prescribed daily frequency or number of occurrences, the second prescribed daily frequency or number of occurrences being less than the first prescribed daily frequency or number of occurrences by a prescribed amount, within a second window following replacement of the target part in that device;
   transform the subset of the logged event data into a normalized form at least in part by determining and storing a count of occurrences of logged events per day for each of a plurality of event types associated with predicting failure of the target part for each device on each of a plurality of days; and
   use the transformed subset of the logged event data to train a machine learning model that can predict failure of the target part in a device based on the current event logs from that device, including by:
      using the transformed subset of the logged event data to generate for each of a plurality of different machine learning algorithms a corresponding candidate machine learning model generated using that machine learning algorithm;
      testing the resulting candidate machine learning models by using each to generate failure predictions based on a test dataset;
      evaluating the respective candidate machine learning models using one or more performance metrics;
      selecting the candidate machine learning model that exhibited the best performance as measured using the one or more performance metrics; and
      deploying the selected candidate machine learning model to predict failure of the target part in a device based on the current event logs from that device.

2. The system of claim 1, further comprising a memory or other data storage device configured to store the log data.

3. The system of claim 1, further comprising a memory or other data storage device configured to store the failure prediction model.

4. The system of claim 1, wherein the processor is further configured to apply the failure prediction model to log data received from said device to generate a failure prediction output for the target part with respect to the device.

5. The system of claim 1, wherein the processor is configured to determine the replacement date based at least in part on the logged data.

6. The system of claim 1, wherein the processor is configured to identify the subset of the logged event data as being associated with impending failure of the target part at least in part by processing the logged event data associated with dates within prescribed ranges before and after the replacement dates to identify event types determined to be associated with predicting failure of the target part.

7. The system of claim 6, wherein the processor is configured to identify said event types determined to be associated with predicting failure of the target part at least in part by determining that occurrence of events of each event type in prescribed windows before and after target part replacement satisfy criteria associated with being a leading indicator of target part failure.

8. The system of claim 1, wherein the processor is configured to generate features for a machine learning algorithm at least in part by aggregating event types associated with impending failure of the target part for each of a plurality of intervals.

9. The system of claim 8, wherein the processor is configured to aggregate event types for each of a plurality of devices over an aggregation interval at least in part by applying a plurality of different aggregation operations, i.e. SUM, AVERAGE, MAX, MIN, etc., on the daily counts of the logged events of each of a plurality of event types associated with impending failure of the target part.

10. The system of claim 9, wherein the processor is configured to create an aggregation interval at least in part by sliding a window of prescribed duration over the events logged by a device ordered by the dates on which those events were logged.

11. The system of claim 1, wherein the processor is configured to use the normalized subset of the logged event data to generate a failure prediction model at least in part by labeling the transformed subset of the logged event data in the normalized form.

12. The system of claim 11, wherein the processor is configured to label the logged data by event group, each event group includes counts of each of a plurality of event types as logged by each device on a given day, and for each event group a label is assigned based at least in part on the number of days between the date with which the event group is associated and the target part replacement date.

13. The system of claim 1, wherein the processor is configured to generate a failure prediction model at least in part by applying a plurality of different machine learning algorithms to the normalized subset of the logged event data.

14. The system of claim 1, wherein the processor is configured to transform the subset of the logged event data into a normalized form at least in part by storing log event data in a format not specific to a device, make, or model of equipment.

15. The system of claim 1, wherein the log data for each of at least a subset of the devices includes unstructured or semi-structured log files for sixty days for a hundred or more devices.

16. The system of claim 1, wherein the processor is configured to determine the respective replacement date on which the target part was replaced in each of at least the subset of the plurality of devices by parsing the log data to determine a part replacement date or last use date, wherein the replacement date or last use date is represented different in devices based on device type, manufacturer, and model.

17. The system of claim 1, wherein the structured dataset comprises log data for each of at least a subset of the devices, at least some of which have dissimilar unstructured log data for events of the same event type, stored in a normalized structured tabular form.

18. The system of claim 1, wherein the selected candidate machine learning model is used to predict failure of the target part in a device based on the current event logs from that device at least in part by receiving unstructured log data from the device, parsing the unstructured log data to extract one or more features associated with the selected candidate machine learning model, and using the model to predict failure of the target part in the device based on the extracted features.

19. A method, comprising:
receiving via a communication interface log data associated with a plurality of devices, the plurality of devices comprising a population of devices of a same device type each having a same target part subject to failure and the log data for each of at least a subset of the devices comprising ten thousand or more logged events per day;
determining based on the received log data, for each of at least a subset of the plurality of devices, a replacement date on which the target part was replaced in that device;
parsing the received log data to generate a structured dataset that includes for each device a plurality of sets of structured event data, each set of structured event data including for an event with which that set of structured event data is associated at least an event severity and an event description;
using the structured dataset to extract from the log data for said plurality of devices a set of structured logged event data with prescribed severity, each logged event in the set having a corresponding event type, the event type being determined at least in part by using a processor to process the event description data comprising the structured dataset to determine that a static portion of the data comprising the event description of the logged event is associated with the event type;
identifying programmatically a subset of the logged event data as being associated with impending failure of the target part, at least in part by determining for each event type with respect to each device in said plurality of devices whether an event of that event type was logged for that device with a first prescribed daily frequency or number of occurrences within a first window before replacement of the target part in that device and determining that events of that event type were logged as having occurred with less than a second prescribed daily frequency or number of occurrences, the second prescribed daily frequency or number of occurrences being less than the first prescribed daily frequency or number of occurrences by a prescribed amount, within a second window following replacement of the target part in that device;
transforming the subset of the logged event data into a normalized format least in part by determining and storing a count of occurrences of logged events per day for each of a plurality of event types associated with predicting failure of the target part for each device on each of a plurality of days; and
using the transformed subset of the logged event data to train a machine learning model that can predict failure of the target part in a device based on the current event logs from that device, including by:
using the transformed subset of the logged event data to generate for each of a plurality of different machine learning algorithms a corresponding candidate machine learning model generated using that machine learning algorithm;
testing the resulting candidate machine learning models by using each to generate failure predictions based on a test dataset;
evaluating the respective candidate machine learning models using one or more performance metrics;
selecting the candidate machine learning model that exhibited the best performance as measured using the one or more performance metrics; and
deploying the selected candidate machine learning model to predict failure of the target part in a device based on the current event logs from that device.

20. The method of claim 19, further comprising applying the failure prediction model to log data received from said device to generate a failure prediction output for the target part with respect to the device.

21. The method of claim 19, wherein the subset of the logged event data is identified as being associated with impending failure of the target part at least in part by processing the logged event data associated with dates within prescribed ranges before and after the replacement dates to identify event types determined to be associated with predicting failure of the target part.

22. A computer program product embodied in a non-transitory computer readable medium, the computer program product comprising computer instructions for:
receiving via a communication interface log data associated with a plurality of devices, the plurality of devices comprising a population of devices of a same device type each having a same target part subject to failure and the log data for each of at least a subset of the devices comprising ten thousand or more logged events per day;
determining for each of at least a subset of the plurality of devices a replacement date on which the target part was replaced in that device;
parsing the received log data to generate a structured dataset that includes for each device a plurality of sets of structured event data, each set of structured event data including for an event with which that set of structured event data is associated at least an event severity and an event description;
using the structured dataset to extract from the log data for said plurality of devices a set of structured logged event data with prescribed severity, each logged event in the set having a corresponding event type, the event type being determined at least in part by using a processor to process the event description data comprising the structured dataset to determine that a static portion of the data comprising the event description of the logged event is associated with the event type;

identifying programmatically a subset of the logged event data as being associated with impending failure of the target part, at least in part by determining for each event type with respect to each device in said plurality of devices whether an event of that event type was logged for that device with a first prescribed daily frequency or number of occurrences within a first window before replacement of the target part in that device and determining that events of that event type were logged as having occurred with less than a second daily prescribed frequency or number of occurrences, the second daily prescribed frequency or number of occurrences being less than the first prescribed daily frequency or number of occurrences by a prescribed amount, within a second window following replacement of the target part in that device;

transforming the subset of the logged event data into a normalized format, least in part by determining and storing a count of occurrences of logged events per day for each of a plurality of event types associated with predicting failure of the target part for each device on each of a plurality of days; and using the transformed subset of the logged event data to train a machine learning model that can predict failure of the target part in a device based on the current event logs from that device, including by:

using the transformed subset of the logged event data to generate for each of a plurality of different machine learning algorithms a corresponding candidate machine learning model generated using that machine learning algorithm;

testing the resulting candidate machine learning models by using each to generate failure predictions based on a test dataset;

evaluating the respective candidate machine learning models using one or more performance metrics;

selecting the candidate machine learning model that exhibited the best performance as measured using the one or more performance metrics; and     deploying the selected candidate machine learning model to predict failure of the target part in a device based on the current event logs from that device.

\* \* \* \* \*